United States Patent
Benson

(10) Patent No.: US 7,318,810 B1
(45) Date of Patent: Jan. 15, 2008

(54) BENSON BIRTHING ROPE FOR AIDING CHILDBIRTH

(75) Inventor: Shirley M. Benson, Drexel, NC (US)

(73) Assignee: Shirley M Benson, Drexel, NC (US)

( * ) Notice: Subject to any disclaimer, the term of this patent is extended or adjusted under 35 U.S.C. 154(b) by 105 days.

(21) Appl. No.: 10/629,996

(22) Filed: Jul. 29, 2003

Related U.S. Application Data

(60) Provisional application No. 60/412,241, filed on Sep. 20, 2002.

(51) Int. Cl.
*A63B 21/002* (2006.01)
*A61B 17/42* (2006.01)

(52) U.S. Cl. ..................... 601/45; 482/91; 482/140; 482/907

(58) Field of Classification Search ............... 482/91, 482/140, 121, 122, 124, 125, 126, 62, 63, 482/93, 94, 109, 129, 111, 53, 112, 907; 87/8; 601/49
See application file for complete search history.

(56) References Cited

U.S. PATENT DOCUMENTS

| | | | | |
|---|---|---|---|---|
| 2,009,655 A | * | 7/1935 | Freymann ............ | 601/45 |
| 2,951,702 A | * | 9/1960 | Goodwin ............ | 482/127 |
| 3,068,002 A | * | 12/1962 | Blane ............... | 482/91 |
| 5,234,392 A | * | 8/1993 | Clark ............... | 482/54 |
| 5,674,159 A | * | 10/1997 | Davidson ............ | 482/92 |
| 6,770,015 B2 | * | 8/2004 | Simonson ............ | 482/99 |
| 2004/0053756 A1 | * | 3/2004 | Tremayne ........... | 482/126 |
| 2004/0069132 A1 | * | 4/2004 | Knudsen et al. ....... | 87/1 |

* cited by examiner

*Primary Examiner*—Danton DeMille

(57) ABSTRACT

A device for assisting in the active and pushing stages of childbirth. The childbirthing device consist of a first loop that can be used to provide resistance for pulling. The first loop is then connected by means of a length of rope to a braided handhold two wrist loops attached thereto. A pregnant person can then insert her hands through the wrist loops and grasp the braided handhold. She can then pull against tension that is applied to the other end of the rope. The pulling action while pushing redirects where the pushing takes place in the pregnant persons body and increases the effectiveness of her "pushing". This decreases the time necessary for the fetus to descend through the birth canal. The wrist loops provide support to the person who might be holding the first loop, on the opposite end of the rope. In case the pregnant person suddenly releases the braided gripping knot the support person won't descend to the ground or fall backwards.

3 Claims, 3 Drawing Sheets

BENSON BIRTHING ROPE FOR AIDING CHILDBIRTH

CROSS REFERENCE TO RELATED APPLICATION

This application claims the benefit of U.S. Provisional Application No. 60/412,241, filed on Sep. 20, 2002.

BACKGROUND OF THE INVENTION

1) Field of the Invention

The present invention relates generally to devices that are helpful in the active labor and pushing stages of childbirth. In particular, the present invention relates to a device that increases the strength of the uterine contraction, increases the interabdominal pressure, and positions the mother so as to align the birthing canal for easier delivery. Specifically, the present invention relates to a device wherein the mother pulls a handhold unit toward her abdomen, working against an opposing force in order to strengthen the uterine contractions.

2) Prior Art

There are presently three basic types of devices that can be used to aide in the birthing process. All of these are very invasive and work at overcoming the body's natural forces during childbirth. These devices—forceps, vacuum cups, and noose-type apparatuses—are used in assisting delivery when the mother's parturient force is not sufficient to expel the fetus, or when there is a need to maneuver the fetus for delivery. Because all of these devices attach to the baby's head, they provide potentially dangerous compression, pulling, and suction forces. At a minimum, these forces can cause unsightly bruising to the fetus. At worst, they can cause lifelong injuries to the child.

Despite advances in the use of forceps, the basic forces acting on the fetal head have remained the same. These are used to maneuver the fetus in to a better orientation for birthing or to assist in expelling the fetus from the birth canal. A compression force about the baby's head between the two blades of the forceps is provided in an amount that is sufficient to overcome the resistant forces of delivery. Excessive compression of the baby's head can cause trauma to the fetus and possibly the mother.

Vacuum cup devices also work to on the principle of overcoming the forces that are employed by the mother's body. The cup is placed on the fetus' head, and the air within the cup is then extracted. A portion of the head tends to be drawn up into the cup, which provides the necessary gripping force for extraction of the baby. This can easily result in the rupture of small blood vessels in the fetal scalp, and possible damage to the fetal head. In addition, there is a danger of maternal lacerations and bruising should the maternal interior gets caught between vacuum cup and the fetal head.

Noose-type devices have not been used in practice due to the risk of fetal trauma that is associated with them. The increased risk of lacerations and permanent damage due to asphyxiation make these devices unsuitable for child delivery.

Additionally, none of these delivery devices provide any help during the active and pushing stages of labor. Forceps and/or vacuums can only be used once the fetus has descended low enough into the birth canal that it can be seen visually, which is generally well towards the end of the labor process, after the majority of the active/pushing time period has past. Taken together, the active and the pushing stages can often last in excess of six hours. During this time, the mother is usually in considerable discomfort due to the strong contraction of the uterus, and can become quite exhausted from the long pushing process.

The fetus is pushed through the birth canal due to the contractions of the uterus. With each contraction, the force of the uterus—combined with the force of the mother's abdominal muscles if she is actively pushing—exerts pressure on the fetus, forcing it to move further down through the birth canal. The time required for the baby to move through the birth canal to the vaginal opening varies, depending on the strength of the contractions and abdominal pressure, the length and diameter of the birth canal, and the amount of stretching that the canal is capable of undergoing. Most all of these are dependent on the mother's specific anatomy. However, interabdominal pressure and uterine contraction strength can be increased utilizing proper pushing techniques and body posturing.

In spite of the teachings and devices available in the prior art, there remains a need to provide a noninvasive aide to the child birthing process that does not substantially increase the risk of trauma to the mother and/or the fetus. There remains a need to provide a noninvasive aide that works with the mother's natural body forces in expelling the baby. There also remains a need to provide an aide that can help to shorten the active and pushing stages of the labor process.

SUMMARY OF THE INVENTION

The present invention relates to a birthing aide that decreases the duration of the active and pushing stages of the labor process by increasing the force exerted by the abdominal muscles and uterine contractions so that the fetus is naturally moved through the birth canal at a faster rate of descent.

The birthing aide of the present invention may be produced from a variety of materials, and can have a number of different configurations. However, in each case, there is provided a handle that is integrally connected by a rope or other connecting line to an anchoring mechanism, which in one embodiment can be a second handle. A nurse/spouse/labor coach holds the anchoring end of the rope, and provides static resistance to the mother who is pulling on the other end of the rope. The length of the rope is determined and resistance to the mother's pulling is provided so that when the mother pulls on the rope, she raises slightly from her reclined position hospital bed into a more sitting posture. This increases the interabdominal pressure, much the same as doing a sit-up or "crunch" exercise, such that the act of pushing is more effective. The mother's uterine contraction strength also increases. Tension can be applied to the rope in a direction that opposes the pulling action of the mother, further increasing the abdominal pressure and contraction strength. Additionally, this slightly raised position correctly aligns the mother's cervix and birth canal, further easing the labor process.

In the broadest sense, the present invention relates to a mother's handhold that is integrally connected by way of a connecting line to an anchoring end.

In the broadest sense, the present invention also comprises a mother's handhold that is integrally connected by way of a connecting line to an anchoring end, and a braking mechanism, that prevents a sudden release in the tension of the connecting line should the mother suddenly drop or let go of the mother's handhold.

In the broadest sense, the present invention also concerns a mother's handhold that is integrally connected by way of a connecting line to an anchoring end, and a braking mechanism, wherein the handle, connecting line, anchoring end, and braking mechanism all are produced from the same material.

In the broadest sense, the present invention also concerns a handle that is integrally connected to an anchoring end by way of a connecting line, and a braking mechanism, wherein the connecting line is a rope, the handle is a knot in the rope, the anchoring end is a loop in the rope, and the braking mechanism is two loops that are slipped over the wrists of the mother.

DESCRIPTION OF THE PREFERRED EMBODIMENTS

Although there have been numerous inventions to help in the birthing and delivery process, none has provided an effective non-invasive device that can significantly shorten the long active and pushing stages of labor.

Figure 1:
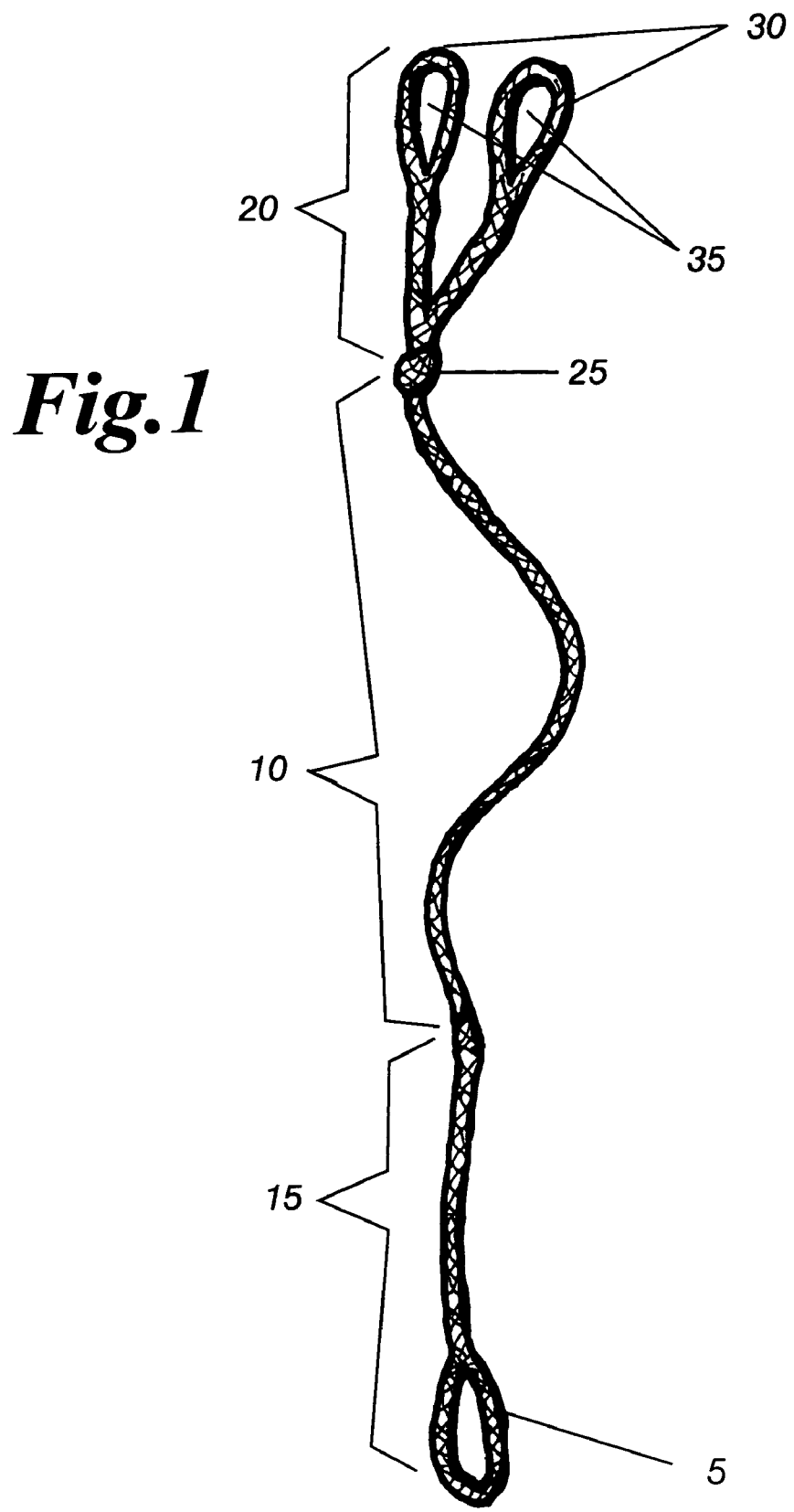
FIG. 1 is view of the presently described child-birthing aide, consistent with the preferred embodiments of the present invention.
Figure 2:
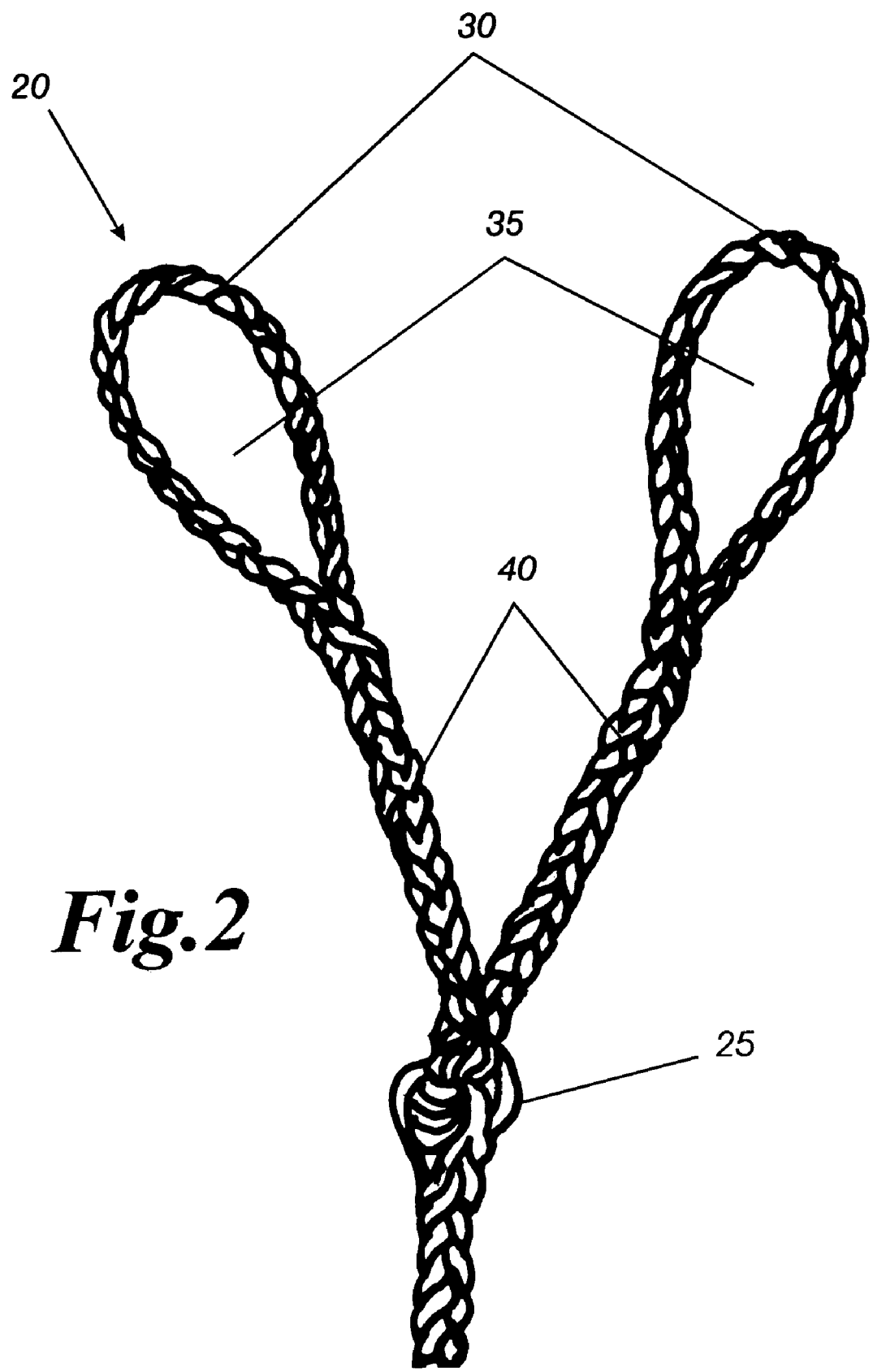
FIG. 2 is an enlargement of the mother's end of the presently described child-birthing aide, consistent with the preferred embodiments of the present invention.
Figure 3:
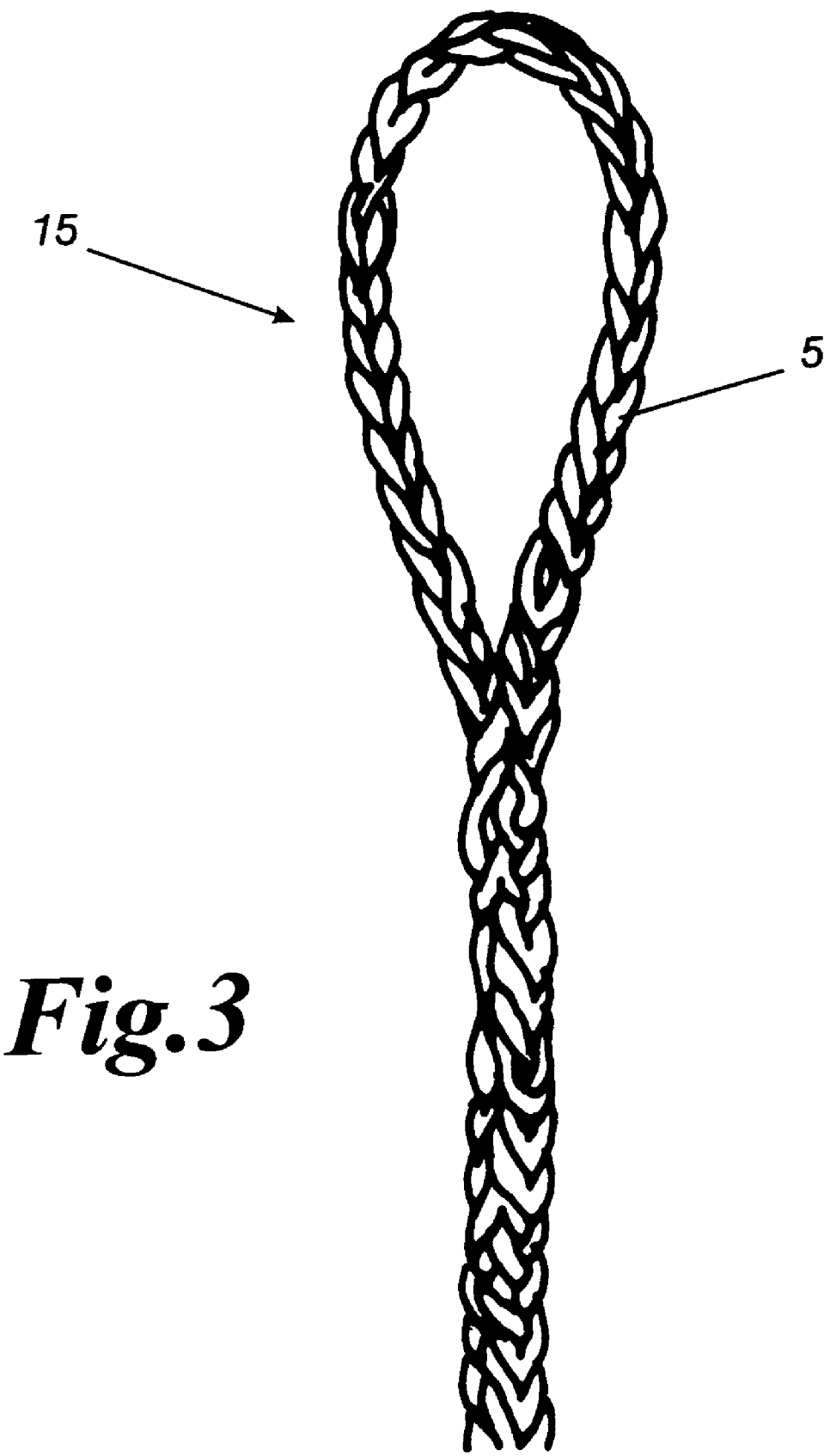
FIG. 3 is an enlargement of the anchoring end of the presently described child-birthing aide, consistent with the preferred embodiments of the present invention.

Referring to FIGS. 1-3, the birthing aide of the present invention is comprised of an anchoring unit (5), a connecting line (10) having an anchoring end (15) and a mother's end (20), and a mother's handhold (25). The anchoring unit (5) is integrally attached to the connecting line (10) at the anchoring end (15), and the mother's handhold (25) is integrally attached to the connecting line (10) at the mother's end (20). The anchoring unit (5) can be securely fastened to a source of resistance that can oppose any pulling action by the mother. In one preferred embodiment, the anchoring end (15) is a loop that is constructed of the same material as the connecting line (10) and the mother's handhold (25). The loop can be held by a spouse, nurse, or birthing coach who can then provide the source of resistance by pulling on the loop. Optionally, the loop can be connected to a stationary object that would resist pulling by the mother at the mother's end (20) of the invention. The stationary object could be a wall, a dresser, or any other heavy object capable of receiving the loop or other anchoring means, and additionally capable of withstanding the pulling force exerted by the mother during the active stages of labor.

The anchoring unit (5) is integrally connected to a connecting line (10) at the anchoring end (15). In a preferred embodiment, this connecting line (10) is made of rope, preferably having a diameter between ⅛ and 1 inches, particularly preferable between ¼ and ¾ inches, optimally ⅜ inches, and can be an extension of the loop that was used as the anchoring end (15). In a particularly preferred embodiment, the rope of the connecting line (10), and a preferred loop of the anchoring unit (5) are woven from liquid crystal polymer fibers. Such fibers are produced by Celanese under the trade name Vectran©. These fibers provide a very high modulus and tenacity, and also maintain a soft feel when held by the mother, or when the optional braking loops are placed around her wrists.

Integrally attached to the mother's end (20) of the connecting line (10) is the mother's handhold (25) of the birthing aide. The mother's handhold (25) is comprised of a handle or other gripping device that the mother pulls towards her abdomen in a direction opposing that of the resistance provided by the anchoring unit (5). In a preferred embodiment, the mother's handhold (25) can be a knot or gripping knob that is tied in or woven into the rope of the connecting line (10). Particularly preferred, the knot or gripping knob is composed of the same material as the connecting line (10). The knot or gripping knob has a diameter of preferably between 1 and 2 inches, preferably between 1½ and 1¾ inches. The mother can then hold onto the gripping knob, or onto the rope just above the gripping knob, such that the gripping knob provides a brace so that her hands cannot easily slip down the rope.

Optionally the birthing aide can further comprise a braking mechanism (30), preferably attached at the mother's end (20), which prevents the sudden release of tension in the connecting line (10). This is beneficial in the preferred embodiment where another person, such as a spouse, nurse or midwife, is providing static resistance at the anchoring end (15) to the pulling action of the mother at the mother's end (20). Often at the end of a contraction, the mother will suddenly let go of the knot handle. When this happens, the person at the anchoring end (15), who was previously working against the force exerted by the mother, is suddenly pulling on a rope that has no resistance from the other end. This can cause the person at the anchoring end (15) to lose his or her balance, resulting in a possible injurious fall to the nurse/midwife/spouse. To prevent this, the current invention contemplates a braking mechanism (30) that is integrally attached to the birthing aide, such that if the mother were to suddenly release her grip of the mother's end (20) handle, tension in the connecting line (10) would be lessened to zero in a more gradual decline.

In a preferred embodiment, the braking mechanism (30) is a pair of wrist loops that are integrally attached to the birthing aide, and preferably attached to the mother's end (20) just below the mother's handhold (25). In this preferred embodiment, the pair of wrist loops is formed from the same rope fiber as that of the connecting line (10) and the anchoring end (15). Particularly preferred, the wrist loops measure 5½ inches in length on the inside of each eyelet (35), and are spliced back into their respective V-arms (40). The V-arms (40) then are spliced back into the connecting line (10) approximately 12 inches from the loop eyelets (35), terminating at the mother's handhold (25). The mother slips her hands through the loops before grasping the mother's handhold (25). When the wrist loops are worn in this fashion, should the mother suddenly release her grasp on the mother's handhold (25), tension in the rope would not immediately decrease to zero. Rather, the loops catch momentarily on the wrists of the mother, providing a quick "step down" in the tension of the rope. This "step down" in tension is just long enough to allow a person at the anchoring end (15) of the rope to regain their own balance that they might have lost due to the mother's sudden release of the birthing aide, preventing injury due to a fall that might otherwise have taken place.

One skilled in the art would realize that many substitutions could be made to the components of the above described preferred embodiments, and that these substitutions would still fall within the contemplated spirit and scope of the present invention. While described in terms of one particular embodiment, it should be recognized that in the invention also contemplates the following as a nonexhaustive list of possible substitutions that can be made.

The anchoring unit (5) has been described in a preferred embodiment as a loop. Alternatively, the anchoring end (15) can consist of a loop, a clip, a screw, snap, tie-down, hook, carabiner, or other device or attachment apparatus that can be connected to an object to provide a source of tension or resistance. Additionally, other items or objects can be attached to the end of the anchoring end (15) to provide an opposing or resisting force to the pulling action of the mother. As stated, this can be a person, a heavy piece of furniture, a wall, or any other heavy stationary item that can resist the mother's pulling action. Additionally, the anchoring end (15) can be attached to a system of weights or counterbalances, so that the force opposing the mother is the action of gravity on some heavy object. In another embodiment of the invention, the anchoring end (15) can consist of a spring providing a resisting force to the mother's pulling that is attached to one of the afore mentioned objects. Other objects that can provide resistant forces, such as hydraulic mechanisms and the like, are also contemplated.

The connecting line (10) has been described in one preferred embodiment as being composed of liquid crystal polymer fibers, however one skilled in the art would realize that this is just one example of the fibers that can be used to construct not only the connecting line (10), but also the anchoring end (15), the mother's end (20), and any attachments thereto such as the wrist loop braking mechanism. Such fibers can include, but are not limited to, natural fibers such as cotton, jute, flax, hemp, abaca, sisal, or henequen, and synthetic fibers including nylons, polyesters, polyolefins such as polypropylene or polyethylene, specifically polyethylene terephthalate, as well as the recited liquid crystal polymers such as Vectran© and any combination of the above fibers, as well as other materials, such as chains, cables and the like. Additionally, the connecting line (10) can be made from bungee cord to provide an increased resistant force to the mother's pulling of the mother's end (20).

The mother's handhold (25) at the mother's end (20) is described in the preferred embodiment as being a knot in the connecting line (10). However, one skilled in the art would recognize that the numerous equivalents that could be used to help the mother maintain a grip on the birthing aide, such as handlebars, molded rubber or plastic handgrips, or large beads or balls that can be incorporated onto or into the birthing aide.

Optionally, the birthing aide can additionally comprise a braking method to prevent the sudden release of tension in the connecting line (10) in the event that the mother releases the handhold. The preferred embodiment described this as a pair of wrist loops, but a variety of equivalents and substitutions would be recognized by one of ordinary skill in the art, including other tie downs or attachments that can be connected to other relatively stationary objects such that the sudden release of tension in the connecting line (10) normally associated with a release of the handle by the mother can be prevented.

Thus it has been apparent that there has been provided, in accordance with the invention, a device for aiding in the birthing process, specifically the active and pushing stages of labor, that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly it is intended to embrace all such alternatives, modifications, and variations as fall within the spirit and broad scope of the appended claims.

What is claimed is:

1. A method for lessening the duration of the active labor and pushing stages of childbirth, said method comprising:
   Providing a birthing aide, said birthing aide comprising entirely of an elongated cord having a mother's end and an aide's end, said mother's end comprises a handhold knot and a pair of arms extending from the handhold knot, each arm terminating in a wrist loop, said aide's end comprises at least one loop;
   The aide providing a source of resistance at the aide's end of the cord;
   The mother inserts her hands through the wrist loops allowing the wrist loops to hang loosely about the wrists;
   The mother grasps both hands about the handhold knot;
   The mother pulls tension against the source of resistance so that the force exerted by the mother's perineal and rectal muscles are increased;
   Wherein the wrist loops provide no support for the mother, said wrist loops will catch momentarily on the wrists of the mother should the mother loose grip providing a quick step down in the tension of the rope.

2. The method of claim 1 wherein said elongated cord is made from rope.

3. The method of claim 2 wherein said rope is made from natural fibers or synthetic fibers, or a mixture thereof.

* * * * *